US009505702B2

(12) United States Patent
Becker et al.

(10) Patent No.: US 9,505,702 B2
(45) Date of Patent: Nov. 29, 2016

(54) INTEGRATED PROCESS FOR THE PRODUCTION OF METHYL ACETATE AND METHANOL FROM SYNTHESIS GAS AND DIMETHYLETHER

(71) Applicant: BP Chemicals Limited, Middlesex (GB)

(72) Inventors: Edo Johann Becker, East Yorkshire (GB); Timothy Crispin Bristow, East Yorkshire (GB)

(73) Assignee: BP CHEMICALS LIMITED, Middlesex (GB)

( * ) Notice: Subject to any disclaimer, the term of this patent is extended or adjusted under 35 U.S.C. 154(b) by 0 days.

(21) Appl. No.: 14/650,921

(22) PCT Filed: Dec. 19, 2013

(86) PCT No.: PCT/EP2013/077473
§ 371 (c)(1),
(2) Date: Jun. 10, 2015

(87) PCT Pub. No.: WO2014/096246
PCT Pub. Date: Jun. 26, 2014

(65) Prior Publication Data
US 2015/0329465 A1 Nov. 19, 2015

(30) Foreign Application Priority Data
Dec. 21, 2012 (EP) ..................... 12199092

(51) Int. Cl.
*C07C 67/37* (2006.01)
*C07C 51/347* (2006.01)
*C07C 29/154* (2006.01)
*C07C 29/151* (2006.01)

(52) U.S. Cl.
CPC ............. *C07C 67/37* (2013.01); *C07C 29/154* (2013.01); *C07C 29/1516* (2013.01); *C07C 29/1518* (2013.01); *C07C 51/347* (2013.01); *Y02P 20/125* (2015.11)

(58) Field of Classification Search
CPC ...... C07C 67/37; C07C 29/151; C07C 41/16
See application file for complete search history.

(56) References Cited

U.S. PATENT DOCUMENTS

2010/0121098 A1* 5/2010 Ditzel ................. B01J 29/20
560/232
2011/0319654 A1* 12/2011 Hazel ................. C07C 67/37
560/232

FOREIGN PATENT DOCUMENTS

| EP | 0 566 370 A2 | | 10/1993 |
| EP | 0566370 A2 | * | 10/1993 |
| GB | 1306863 | * | 2/1973 |

* cited by examiner

*Primary Examiner* — Paul A Zucker
(74) *Attorney, Agent, or Firm* — Nixon & Vanderhye P.C.

(57) ABSTRACT

Integrated process for the production of methyl acetate and methanol. The process is carried out by carbonylating dimethyl ether with synthesis gas and recovering methanol and unreacted synthesis gas. The recovered synthesis gas is utilized as the sole fresh synthesis gas for methanol synthesis.

29 Claims, 4 Drawing Sheets

INTEGRATED PROCESS FOR THE PRODUCTION OF METHYL ACETATE AND METHANOL FROM SYNTHESIS GAS AND DIMETHYLETHER

This application is the U.S. national phase of International Application No. PCT/EP2013/077473 filed Dec. 19, 2013 which designated the U.S. and claims priority to European Patent Application No. 12199092.3 filed Dec. 21, 2012, the entire contents of each of which are hereby incorporated by reference.

The present invention relates to an integrated process for the production of methyl acetate and methanol from synthesis gas and dimethyl ether.

BACKGROUND OF THE INVENTION

Methanol is primarily used to produce formaldehyde, methyl tertiary butyl ether (MTBE) and acetic acid, with smaller amounts going into the manufacture of dimethyl terephthalate (DMT), methylmethacrylate (MMA), chloromethanes, methylamines, glycol methyl ethers, and fuels. It also has many general solvent and antifreeze uses, such as being a component for paint strippers, car windshield washer compounds and a de-icer for natural gas pipelines A major use of methyl acetate is as a low toxicity solvent in glues, paints and a broad range of coating and ink resin applications. Methyl acetate also finds use as a feedstock in the production of acetic anhydride.

Methanol may be produced on a commercial basis by the conversion of synthesis gas containing carbon monoxide, hydrogen and optionally carbon dioxide over a suitable catalyst according to the overall reaction:

$$2H_2 + CO \leftrightarrows CH_3OH$$

Widely used catalysts for methanol synthesis from synthesis gas are based on copper.

Methyl acetate may be produced, as described, for example, in WO 2006/121778, by carbonylating dimethyl ether with carbon monoxide in the presence of a zeolite carbonylation catalyst, such as a mordenite zeolite.

The production of methyl acetate by the carbonylation of dimethyl ether may also be carried out using mixtures of carbon monoxide and hydrogen, as described, for example, in WO 2008/132438. According to WO 2008/132438, the molar ratio of carbon monoxide:hydrogen for use in the carbonylation step may be in the range 1:3 to 15:1, such as 1:1 to 10:1, for example 1:1 to 4:1.

WO 01/07393 describes a process for the catalytic conversion of a feedstock comprising carbon monoxide and hydrogen to produce at least one of an alcohol, ether and mixtures thereof and reacting carbon monoxide with the at least one of an alcohol, ether and mixtures thereof in the presence of a catalyst selected from solid super acids, heteropolyacids, clays, zeolites and molecular sieves, in the absence of a halide promoter, under conditions of temperature and pressure sufficient to produce at least one of an ester, acid, acid anhydride and mixtures thereof U.S. Pat. No. 5,286,900 relates to a process for preparing an acetic acid product selected from acetic acid, methyl acetate, acetic anhydride and mixtures thereof by conversion of a synthesis gas comprising hydrogen and carbon oxides, said process comprising the steps of: (i) introducing synthesis gas into a first reactor at a pressure of 5-200 bar and a temperature of 150-400° C., and catalytically converting the synthesis gas into methanol and dimethyl ether and (ii) carbonylating the methanol and dimethyl ether formed in step (i) by passing the entire effluent from the first reactor to a second reactor and carbonylating therein, at a pressure of 1-800 bar and a temperature of 100-500° C. in the presence of a catalyst, the methanol and dimethyl ether to an acetic acid product.

EP-A-0566370 describes a process for the production of ethylidene diacetate, acetic acid, acetic anhydride and methyl acetate directly from synthesis gas via an intermediate product stream containing dimethyl ether. Dimethyl ether is produced from synthesis gas in a first liquid phase reactor and the reactor effluent comprising dimethyl ether, methanol and unreacted synthesis gas flows to a second liquid phase reactor containing acetic acid in which the oxygenated acetyl compounds are synthesized catalytically. Vinyl acetate and additional acetic acid optionally are produced by pyrolysis of ethylidene diacetate in a separate reactor system. Synthesis gas is preferably obtained by partial oxidation of a hydrocarbon feedstock such as natural gas. Optionally a portion of the acetic acid co-product is recycled to the partial oxidation reactor for conversion into additional synthesis gas.

Synthesis gas comprises carbon monoxide and hydrogen. Optionally carbon dioxide is included. The synthesis gas ratio or stoichiometric number (SN) of a synthesis gas composition is conventionally calculated as

$$SN = (H_2 - CO_2)/(CO + CO_2)$$

wherein $H_2$, CO and $CO_2$ represent the composition of the gas on a molar basis.

Desirably, the optimum stoichiometric number of a synthesis gas for use in methanol production is 2.05. Typically, however, processes for the production of methyl acetate by the carbonylation of dimethyl ether with synthesis gas employ synthesis gas with a stoichiometric excess of carbon monoxide. Thus a major drawback in carbonylation and methanol synthesis processes is that the hydrogen:carbon monoxide ratios desirable for methanol synthesis are significantly higher than the desired ratios for carbonylation.

A further drawback of processes for the carbonylation of dimethyl ether is that a purge gas must be removed from the process to prevent recycle components from reaching unacceptable levels in the reactor. Typically, purge gases are disposed of by burning. Purge gas from the carbonylation process contains carbon monoxide and invariably contains some dimethyl ether and methyl acetate. Therefore, the removal of these components by purging represents a loss of values and reduces the overall efficiency of the process.

As described above, processes for the carbonylation of dimethyl ether with synthesis gas typically employ synthesis gas with a stoichiometric excess of carbon monoxide. This results in unconsumed carbon monoxide being withdrawn (together with hydrogen which generally remains unconsumed in the process) from the process as part of the carbonylation product stream. Typically, to avoid loss of carbon monoxide feedstock from the process, it is recycled to the carbonylation reactor together with the unconsumed hydrogen. A disadvantage of this is that hydrogen builds-up in the reactor and an undesirable reduction in the carbonylation reaction rate is observed.

A further drawback is that it has now been found that processes for the carbonylation of dimethyl ether in the presence of zeolite catalysts suffer from the undesirable formation of certain low-boiling by-products, including olefins, for example ethylene and $C_2$ oxygenate compounds, such as acetone and acetaldehyde. Recycling streams containing these low-boiling by-products to the carbonylation process causes a reduction in the carbonylation catalyst lifetime and an increase in the level of by-products formed in the carbonylation process.

Furthermore, due to difficulties associated with the transport and storage of synthesis gas, it is typically generated in situ. Thus, a significant expense for new methyl acetate and methanol production capacity is the capital and operating costs associated with synthesis gas generation.

SUMMARY OF THE INVENTION

It has now been found that the above-described problems may be overcome or at least mitigated by integrating a process for the production of methyl acetate by the carbonylation of dimethyl ether with a methanol synthesis process; which integrated process uses a synthesis gas feed to the carbonylation reaction without the need for an additional synthesis gas feed for methanol synthesis.

Accordingly, the present invention provides an integrated process for the production of methyl acetate and methanol which process comprises:
(i) feeding synthesis gas and dimethyl ether into a carbonylation reaction zone and reacting therein the synthesis gas and dimethyl ether in the presence of a carbonylation catalyst to form a gaseous carbonylation reaction product comprising methyl acetate and a hydrogen-enriched synthesis gas;
(ii) withdrawing carbonylation reaction product from the carbonylation reaction zone and recovering from at least a portion of the carbonylation reaction product a methyl acetate-rich liquid stream and a synthesis gas stream; and
(iii) passing at least a portion of the synthesis gas stream recovered from the carbonylation reaction product to a methanol synthesis zone and contacting it therein with a methanol synthesis catalyst to form a methanol synthesis product comprising methanol and unconverted synthesis gas.

Advantageously, the present invention provides a process for the production of both methyl acetate and methanol from synthesis gas whilst minimizing loss of valuable carbon monoxide feedstock from methyl acetate production. Unreacted carbon monoxide and hydrogen present in a carbonylation reaction stream is usefully converted to methanol in the methanol synthesis zone thereby eliminating the need for an additional source of synthesis gas for methanol synthesis.

Advantageously, the present invention provides a process which allows for the reduction or complete elimination of the need to dispose of purge gas vented from a process for the carbonylation of dimethyl ether with carbon monoxide in the presence of a catalyst to produce methyl acetate.

Advantageously, the present invention provides a process which enhances zeolite carbonylation catalyst lifetime and/or catalytic performance by avoiding the need to recycle to the carbonylation reaction low-boiling carbonylation by-products such as olefins and $C_2$ oxygenate compounds and/or the build-up of recycle hydrogen.

Desirably, the present invention allows methanol to be produced from a synthesis gas feed which has a stoichiometric number which is sub-optimal for methanol production whilst also allowing the production of methyl acetate.

Furthermore, the present invention allows the production of methanol whilst avoiding or mitigating the need for imported carbon dioxide thereby reducing methanol process costs.

BRIEF DESCRIPTION OF THE DRAWINGS

The accompanying drawings, which are incorporated in and constitute part of the specification, illustrate embodiments of the invention and, together with the description, serve to explain the features, advantages, and principles of the invention. In the drawings.

Figure 1:
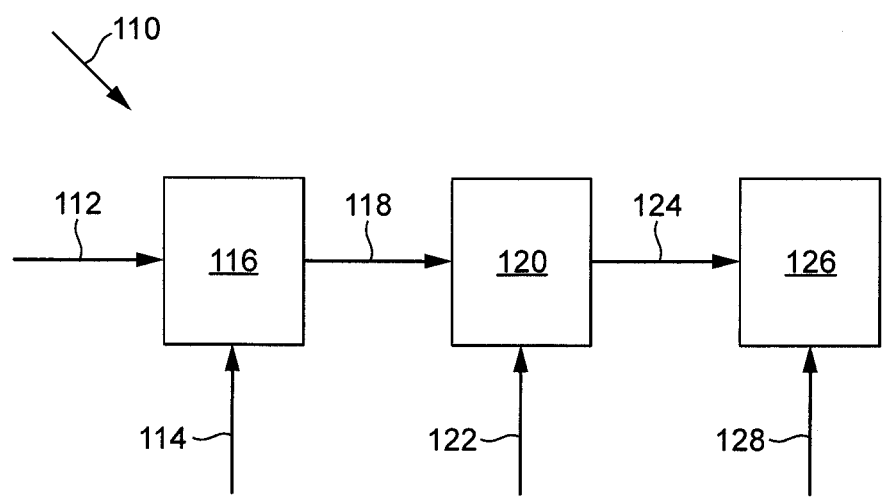
FIG. 1 is a block diagram showing one embodiment of the present invention of an integrated process for the production of methyl acetate and methanol.

As discussed above, synthesis gas comprises carbon monoxide and hydrogen. Optionally, synthesis gas may also comprise carbon dioxide. Typically, synthesis gas may also comprise small amounts of inert gases such nitrogen and methane. Conventional processes for converting hydrocarbon sources to synthesis gas include steam reforming and partial oxidation. Examples of hydrocarbon sources used in synthesis gas production include bio-mass, natural gas, methane, $C_2$-$C_5$ hydrocarbons, naphtha, coal and heavy petroleum oils.

Steam reforming generally comprises contacting a hydrocarbon with steam to form synthesis gas. The process preferably includes the use of a catalyst, such as those based on nickel.

Partial oxidation generally comprises contacting a hydrocarbon with oxygen or an oxygen-containing gas such as air to form synthesis gas. Partial oxidation takes place with or without the use of a catalyst, such as those based on rhodium, platinum or palladium.

In the present invention, synthesis gas comprising carbon monoxide and hydrogen and dimethyl ether is reacted in a carbonylation reaction zone in the presence of a suitable carbonylation catalyst to produce a gaseous carbonylation reaction product comprising methyl acetate and synthesis gas enriched in hydrogen.

Suitably, the synthesis gas feed to the carbonylation reaction zone is synthesis gas generated by the steam reforming of hydrocarbons or by the partial oxidation of hydrocarbons. Preferably the synthesis gas is generated by the partial oxidation of natural gas or methane Suitably, the synthesis gas formed in the synthesis gas generating process is cooled prior to being introduced to the carbonylation reaction zone. Preferably, the synthesis gas is cooled so as to condense at least a portion of the water vapour formed during the synthesis gas forming process.

Synthesis gas supplied to the carbonylation reaction zone is preferably a dry synthesis gas. Water may be removed from synthesis gas, using any suitable means, for example a molecular sieve.

The synthesis gas feed to the carbonylation reaction zone comprises fresh synthesis gas. For the present purposes, fresh synthesis gas includes stored sources of synthesis gas. Suitably, the synthesis gas consists essentially of fresh synthesis gas that is in the absence of any recycle synthesis gas.

The stoichiometric number (SN) of a fresh synthesis gas is not critical and may vary significantly. Desirably, to provide a suitable synthesis gas composition to the methanol synthesis zone for the stoichiometrically balanced production of methanol, the fresh synthesis gas contains at least a partial excess of hydrogen compared to carbon monoxide and carbon dioxide. Suitably, therefore, a fresh synthesis gas has a stoichiometric number in the range 0.9 to 1.3, preferably in the range 1.0 to 1.2, for example in the range 1.0 to 1.1.

Preferably, the fresh synthesis gas comprises carbon dioxide. Carbon dioxide may be present in the fresh synthesis gas in an amount of not greater than 50 mol %, such as in the range 0.5 to 12 mol %.

Suitably, the synthesis gas feed to the carbonylation reaction zone may also comprise recycle synthesis gas. Recycle synthesis gas streams can be one or more gaseous or liquid streams comprising carbon monoxide, hydrogen and optionally carbon dioxide which are recovered from any part of the process downstream of the carbonylation reaction. Suitable recycle synthesis gas streams include synthesis gas recovered from the carbonylation reaction product.

In an embodiment of the present invention, the synthesis gas feed to the carbonylation reaction zone comprises a mixture of fresh synthesis gas and recycle synthesis gas. Suitably, the synthesis gas comprises a mixture of fresh synthesis gas and synthesis gas recovered from the carbonylation reaction product. Preferably, the mixture of fresh synthesis gas and the synthesis gas recovered from the carbonylation reaction product comprises carbon dioxide. Carbon dioxide may be present in the mixture of fresh synthesis gas and synthesis gas recovered from the carbonylation reaction product in a total amount of not greater than 50 mol %, such as in the range 0.5 to 12 mol %.

Synthesis gas may be fed into the carbonylation reaction zone as one or more feed streams. The one or more streams may be either fresh synthesis gas or a mixture of fresh and recycle synthesis gas.

Preferably, prior to use in the carbonylation reaction, the synthesis gas (whether fresh or a mixture of fresh and recycle) is heated, for example in one or more heat exchangers, to the desired carbonylation reaction temperature.

The carbon monoxide partial pressure in the carbonylation reaction zone should be sufficient to permit the production of methyl acetate. Thus, suitably, the carbon monoxide partial pressure is in the range 0.1 to 100 barg (10 kPa to 10,000 kPa), such as 10 to 65 barg (1000 kPa to 6500 kPa).

The hydrogen partial pressure in the carbonylation reaction zone is suitably in the range 1 barg to 100 barg (100 kPa to 10,000 kPa), preferably 10 to 75 barg (1000 kPa to 7500 kPa).

The dimethyl ether feed to the carbonylation reaction zone may be fresh dimethyl ether or a mixture of fresh and recycle dimethyl ether. Suitably, recycle streams to the carbonylation reaction zone comprising dimethyl ether may be obtained from any part of the process downstream of the carbonylation reaction including, for example, the hydrogen-enriched synthesis gas recovered from the carbonylation reaction product.

Dimethyl ether may be fed to the carbonylation reaction zone as one or more fresh dimethyl ether streams or as one or more streams comprising a mixture of fresh and recycle dimethyl ether.

Dimethyl ether and synthesis gas may be introduced into the carbonylation reaction zone as one or more separate streams but preferably are introduced as one or more combined synthesis gas and dimethyl ether streams.

In an embodiment, the dimethyl ether and synthesis gas are fed into the carbonylation reaction zone as a combined stream, which combined stream is heated to the desired carbonylation reaction temperature, for example in one or more heat exchangers, prior to use in the carbonylation reaction zone.

In commercial practice, dimethyl ether is produced by the catalytic conversion of methanol over methanol dehydration catalysts. This catalytic conversion results in a product which is predominantly dimethyl ether but it may also contain low levels of methanol and/or water. The presence of significant amounts of water in a zeolite catalysed carbonylation of dimethyl ether tends to inhibit the production of methyl acetate product. In addition, water may be generated in the carbonylation reaction via side-reactions. However, the dimethyl ether for use in the carbonylation reaction of the present invention may contain small amounts of one or more of water and methanol provided that the total amount of methanol and water is not so great as to significantly inhibit the production of methyl acetate. Suitably, the dimethyl ether (including recycles) may contain water and methanol in a total amount in the range 1 ppm to 10 mol %, for example 1 ppm to 2 mol %, such as 1 ppm to 1 mol %, preferably in the range from 1 ppm to 0.5 mol %.

Preferably, the dimethyl ether (fresh and any recycle) feed is dried prior to use in the carbonylation reaction.

The concentration of the dimethyl ether may be in the range of 1 mol % to 20 mol %, suitably in the range 1.5 mol % to 15 mol %, for instance 5 to 15 mol %, for example 2.5 to 12 mol %, such as 2.5 to 7.5 mol %, based on the total of all streams to the carbonylation reaction zone.

The molar ratio of carbon monoxide to dimethyl ether in the carbonylation reaction is suitably in the range 1:1 to 99:1, for example 1:1 to 25:1, such as 2:1 to 25:1.

Carbon dioxide reacts with hydrogen to form water and carbon monoxide. This reaction is commonly referred to as the reverse water gas shift reaction. Thus, where it is desired to utilise synthesis gas comprising carbon dioxide, to mitigate the effect of water on the carbonylation reaction, it is preferred that the carbonylation catalyst is not active for the reverse water-gas shift reaction or for the production of methanol. Preferably, the carbonylation catalyst comprises an aluminosilicate zeolite.

Zeolites comprise a system of channels which may be interconnected with other channel systems or cavities such as side-pockets or cages. The channel systems are defined by ring structures which rings may comprise, for example, 8, 10, or 12 members. Information about zeolites, their framework structure types and channel systems is published in the Atlas of Zeolite Framework Types, C. H. Baerlocher, L. B. Mccusker and D. H. Olson, 6th Revised Edition, Elsevier, Amsterdam, 2007 and is also available on the website of the International Zeolite Association at www.iza-online.org.

Suitably, the carbonylation catalyst is a crystalline aluminosilicate zeolite which comprises at least one channel which is defined by an 8-member ring. The aperture of the zeolite channel system defined by the 8-membered ring should be of such dimensions that the reactant molecules, dimethyl ether and carbon monoxide, can diffuse freely in and out of the zeolite framework. Suitably, the aperture of the 8-member ring channel of the zeolite has dimensions of at least 2.5×3.6 Angstroms. Preferably, the channel defined by the 8-member ring is interconnected with at least one channel defined by a ring with 10 or 12 members.

Non-limiting examples of aluminosilicate zeolites which comprise at least one channel which is defined by an 8-membered ring include zeolites of framework structure type MOR (for example, mordenite), FER (for example, ferrierite), OFF (for example, offretite) and GME (for example, gmelinite).

A preferred carbonylation catalyst is a mordenite zeolite.

The carbonylation catalyst may be a zeolite in its hydrogen form. Preferably, the carbonylation catalyst is mordenite in its hydrogen form.

The carbonylation catalyst may be a zeolite which is fully or partially loaded with one or more metals. Suitable metals for loading onto the zeolite include copper, silver, nickel, iridium, rhodium, platinum, palladium or cobalt and combinations thereof, preferably copper, silver and combinations thereof. The metal loaded form may be prepared by techniques such as ion-exchange and impregnation. These techniques are well-known and typically involve exchanging the hydrogen or hydrogen precursor cations (such as ammonium cations) of a zeolite with metal cations.

The carbonylation catalyst may be a zeolite which, in addition to aluminium and silicon, has present in its framework one or more additional metals such as trivalent metals selected from at least one of gallium, boron and iron. Suitably, the carbonylation catalyst may be a zeolite which contains gallium as a framework element. For example, the carbonylation catalyst may be a mordenite which contains gallium as a framework element, such as a mordenite which contains gallium as a framework element and is in its hydrogen form.

The carbonylation catalyst may be a zeolite which is composited with at least one binder material. As will be appreciated by those of ordinary skill in the art, binder materials are selected such that the catalyst is suitably active and robust under the carbonylation reaction conditions. Examples of suitable binder materials include inorganic oxides, such as silicas, aluminas, alumina-silicates, magnesium silicates, magnesium aluminium silicates, titanias and zirconias. Preferred binder materials include aluminas, alumina-silicates and silicas, for example boehemite type alumina.

The relative proportions of the zeolite and the binder material may vary widely but suitably, the binder material may be present in a composite in an amount in the range of 10% to 90% by weight of the composite, preferably, in the range of 10% to 65% by weight of the composite.

Zeolite powders may also be formed into particles without the use of a binder. Typical zeolite catalyst particles include extrudates whose cross sections are circular or embrace a plurality of arcuate lobes extending outwardly from the central portion of the catalyst particles.

In an embodiment of the present invention, the carbonylation catalyst is a zeolite, such as a mordenite, which is composited with at least one inorganic oxide binder material, which may suitably be selected from aluminas, silicas and alumina-silicates, and is utilised in the form of a shaped body, such as an extrudate. In particular, the carbonylation catalyst is a mordenite composited with an alumina, such as a boehmite alumina. The mordenite composited with the alumina may contain gallium as a framework element.

The silica to alumina molar ratio of the zeolites for use as carbonylation catalysts in the present invention is the bulk or overall ratio. This can be determined by any one of a number of chemical analysis techniques. Such techniques include x-ray fluorescence, atomic absorption and ICP (inductive coupled plasma). All will provide substantially the same silica to alumina molar ratio value.

The bulk silica to alumina molar ratio (herein also termed "SAR") of synthetic zeolites will vary. For example, the SAR of a zeolite, such as mordenite, may range from as low as 5 to over 90.

The SAR of a zeolite for use as a carbonylation catalyst in the present invention may suitably be in the range from 10:1 to 90:1, for example 20:1 to 60:1.

It is preferred that a zeolite carbonylation catalyst is activated immediately before use, typically by heating it at elevated temperature for at least one hour under flowing nitrogen, carbon monoxide, hydrogen or mixtures thereof.

Preferably, the carbonylation reaction is carried out under substantially anhydrous conditions. Suitably therefore, as discussed above, to limit the presence of water in the carbonylation reaction, all reactants, including fresh synthesis gas, fresh dimethyl ether, any recycles thereof, and the catalyst are dried prior to use in the carbonylation reaction. Suitably, the combined amount of water and methanol (a source of water) present in the carbonylation reaction is limited to be in the range 1 ppm to 0.5 mol %, preferably in the range 1 ppm to 0.1 mol %, and most preferably in the range 1 ppm to 0.05 mol %.

Desirably, the combined amount of water and methanol introduced into the carbonylation reaction zone is not more than 0.5 mol %, for example 0 to 0.5 mol %, such as 1 ppm to 0.5 mol %.

The carbonylation catalyst may be employed in a fixed bed carbonylation reaction zone, for example in the shape of pipes or tubes, where the dimethyl ether and synthesis gas feeds, typically in gaseous form, are passed over or through the carbonylation catalyst.

The carbonylation reaction is carried out in the vapour phase.

The synthesis gas and dimethyl ether are reacted in the presence of a carbonylation catalyst under reaction conditions effective to form a gaseous carbonylation reaction product which comprises methyl acetate.

Preferably, the carbonylation reaction is carried out at a temperature in the range of 100° C. to 350° C., for example in the range 250° C. to 350° C.

Preferably, the carbonylation reaction is carried out at a total pressure in the range 1 to 200 barg (100 kPa to 20,000 kPa), for example 10 to 100 barg (1000 kPa to 10,000 kPa), such as 50 to 100 barg (5000 kPa to 10,000 kPa).

In an embodiment, the carbonylation reaction is carried out at temperatures in the range 250° C. to 350° C. and at total pressures in the range 50 to 100 barg (5000 kPa to 10,000 kPa).

In a preferred embodiment, synthesis gas and dimethyl ether, preferably containing water and methanol in not more than a combined amount in the range 1 ppm to 10 mol %, are reacted in the presence of a carbonylation catalyst, such as an aluminosilicate zeolite having at least one channel which is defined by an 8-membered ring, for example mordenite, preferably mordenite in its hydrogen form, at a temperature in the range 100° C. to 350° C., and at a total pressure in the range 10 to 100 barg (1000 kPa to 10,000 kPa), to form a gaseous carbonylation reaction product comprising methyl acetate and synthesis gas enriched in hydrogen.

The dimethyl ether and synthesis gas (optionally comprising carbon dioxide and any recycles) may suitably be fed to the carbonylation reaction zone at a total gas hourly space velocity of flow of gas through the catalyst bed (GHSV) is in the range 500 to 40,000 $h^{-1}$, such as 2000 to 20,000 $h^{-1}$.

Preferably, the carbonylation reaction is carried out substantially in the absence of halides, such as iodide. By the term 'substantially' is meant that the halide, for example the total iodide content of the feed streams to the carbonylation reaction zone, is less than 500 ppm, preferably less than 100 ppm.

The hydrogen present in synthesis gas is essentially inactive in the carbonylation reaction and thus the synthesis gas withdrawn from the carbonylation reaction zone is enriched in hydrogen relative to the hydrogen content of the synthesis gas feed to the carbonylation reaction zone.

The carbonylation reaction product withdrawn from the carbonylation reaction zone comprises methyl acetate and a synthesis gas enriched in hydrogen. The carbonylation reaction product will typically comprise small amounts of additional components such as one or more of unreacted dimethyl ether, water, methanol and inert gases. The carbonylation reaction product may also comprise low-boiling by-products formed via side-reactions in the carbonylation reaction. These by-products are typically one or more of olefins, for example ethylene and $C_2$ oxygenate compounds, such as acetaldehyde and acetone.

Carbon dioxide is generally unconsumed in the carbonylation reaction, thus when the synthesis gas feed to the carbonylation reaction zone comprises carbon dioxide, the carbonylation reaction product will also comprise carbon dioxide.

The carbonylation reaction product is withdrawn from the carbonylation reaction zone in gaseous form.

In the present invention, a methyl acetate-rich liquid stream and a synthesis gas stream are recovered from the withdrawn carbonylation reaction product.

Suitably, the withdrawn carbonylation reaction product is cooled and separated to recover a methyl acetate-rich liquid stream and a synthesis gas stream. The cooling of the carbonylation reaction product may be carried out using one or more heat exchange means, such as conventional heat exchangers, to cool the carbonylation reaction product to, for example, a temperature in the range of 50° C. or less, suitably to a temperature in the range 40° C. to 50° C.

A methyl acetate-rich liquid stream may be recovered from a synthesis gas stream, for example in one or more gas/liquid separation means such as a knock-out drum or a tangential inlet drum.

The methyl acetate-rich liquid stream comprises mainly methyl acetate but may also comprise minor amounts of one or more of unreacted dimethyl ether, methanol, water and dissolved inert gases and synthesis gas.

The synthesis gas stream comprises mainly carbon monoxide, hydrogen and where present in a synthesis gas feed to the carbonylation reaction zone, carbon dioxide. The synthesis gas stream may also comprise minor amounts of one or more of unreacted dimethyl ether, water, methyl acetate, inert gases and low-boiling carbonylation by-products.

Methyl acetate may be recovered from the methyl acetate-rich liquid stream, for example by distillation, and sold as such or used as a feedstock in downstream chemical processes.

In an embodiment, methyl acetate is recovered from at least a portion of the methyl acetate-rich liquid stream and the recovered methyl acetate is converted to acetic acid, preferably by a hydrolysis process. Hydrolysis of the recovered methyl acetate may be carried out using known processes, such as catalytic distillation processes. Typically, in catalytic distillation processes for the hydrolysis of methyl acetate, methyl acetate is hydrolysed with water in a fixed-bed reactor employing an acidic catalyst, such as an acidic ion exchange resin or a zeolite, to produce a mixture comprising acetic acid and methanol from which acetic acid and methanol may be separated by distillation, in one or more distillation stages.

At least a portion of the synthesis gas recovered from the carbonylation reaction product is passed to the methanol synthesis zone for the production of methanol. If desired, the synthesis gas in its entirety may be passed to the methanol synthesis zone. Suitably, the synthesis gas recovered from the carbonylation reaction product is split into two portions wherein a first portion of the synthesis gas is passed to the methanol synthesis zone and at least one other portion, which is for example equal to the first portion, is recycled to the carbonylation reaction zone. Preferably, however, the synthesis gas recovered from the carbonylation reaction product is split into a major portion and a minor portion. More preferably, the synthesis gas is split into a major portion and a minor portion wherein the major portion is recycled to the carbonylation reaction zone and the minor portion is passed to the methanol synthesis zone.

Suitably, the major portion is at least 50 mol % of the synthesis gas recovered from the carbonylation reaction zone, such as in the range 60 to 85 mol %, for example 70 to 80 mol %. Suitably, the minor portion is less than 50 mol %, such as in the range 10 to 30 mol %, for example 20 to 30 mol %.

In one embodiment, 70 to 80 mol % of the synthesis gas recovered from the carbonylation reaction product is recycled to the carbonylation reaction zone and 10 to 30 mol % of the synthesis gas is passed to the methanol synthesis zone.

Suitably, synthesis gas recovered from the carbonylation reaction product may be compressed, in one or more compressors, prior to recycle to the carbonylation reaction zone.

If desired, a portion of the synthesis gas recovered from the carbonylation reaction product can be vented as purge gas but, preferably, substantially all of the synthesis gas is passed to the methanol synthesis zone or recycled to the carbonylation reaction zone or a combination of both.

The stoichiometric number of the synthesis gas recovered from the carbonylation reaction product will depend principally upon the stoichiometric number of the fresh synthesis gas feed to the carbonylation reaction zone and the degree of conversion therein, but it may also be adjusted by varying the amount of synthesis gas recycled to the carbonylation reaction zone. The stoichiometric number of the synthesis gas recovered from the carbonylation reaction zone may therefore be adjusted so as to be optimal for methanol synthesis by adjusting one or more of these factors. Preferably, the synthesis gas recovered from the carbonylation reaction product has a stoichiometric number optimised for methanol synthesis, that is, a stoichiometric number suitably in the range 1.5 to 2.5, such as 2.0 to 2.1, preferably 2.05.

The methanol synthesis process used to manufacture the methanol product stream of the present invention can be any suitable process. Commercially, methanol is produced by the catalytic conversion of carbon monoxide and hydrogen according to the overall equation $CO+2H_2 \leftrightarrows CH_3OH$. The reaction proceeds in accordance with the following reactions:

$$CO_2 + 3H_2 \leftrightarrows CH_3OH + H_2O \quad \text{(I)}$$

$$H_2O + CO \leftrightarrows CO_2 + H_2 \quad \text{(II)}$$

Conventionally, the carbon monoxide and hydrogen required for methanol production is obtained from synthesis gas supplied directly to a methanol reaction zone from reforming or partial oxidation processes. Advantageously, in the present invention, there is utilised a single fresh synthesis gas feed to enable the production of both methyl acetate and methanol. In the present invention, it is not necessary to supply fresh synthesis gas to the methanol synthesis zone in addition to the synthesis gas supplied to the carbonylation reaction zone. As described above, in the present invention, carbon monoxide and hydrogen required for methanol synthesis is obtained from the synthesis gas recovered from the carbonylation reaction product.

In a preferred embodiment, the process of the present invention further comprises the steps of:
(iv) withdrawing methanol synthesis product from the methanol synthesis zone and recovering therefrom a methanol-rich liquid stream and a synthesis gas stream; and
(v) recycling at least a portion of the synthesis gas stream recovered from the methanol synthesis product to the methanol synthesis zone.

The synthesis gas recovered from the carbonylation reaction product may be employed as the sole source of synthesis gas to the methanol synthesis zone. Preferably, however, the synthesis gas for use in methanol synthesis also comprises at least a portion of synthesis gas recovered from the methanol synthesis product. Suitably, therefore, the synthesis gas passed to the methanol synthesis zone is a combined feed of synthesis gas recovered from the carbonylation reaction product and synthesis gas recovered from the methanol synthesis product.

Prior to use in the methanol synthesis zone, the synthesis gas feeds to the methanol synthesis zone such as synthesis gas recovered from the carbonylation reaction product and a combined feed of synthesis gas recovered from the carbonylation reaction product and synthesis gas recovered from the methanol synthesis product, may be heated, for example in one or more heat exchangers, to the desired methanol synthesis temperature.

The synthesis of methanol requires a source of carbon dioxide. Sources of carbon dioxide include synthesis gas, carbon dioxide generated in-situ during methanol synthesis and imported carbon dioxide. Carbon dioxide can be generated in-situ from water formed in the process and by the addition of water to the methanol synthesis. However, there are a number of disadvantages associated with the addition of water to methanol synthesis for in-situ generation of carbon dioxide, including the requirements for additional processing and the provision of a suitable source of water. However, if desired, at least one of water and imported carbon dioxide may be introduced into the methanol synthesis zone. Most desirably, however, all of the carbon dioxide required for methanol synthesis is derived from the synthesis gas feed to the carbonylation reaction or from in-situ generation from water formed in the methanol synthesis process.

Carbon dioxide which is unconsumed in the methanol synthesis is withdrawn from the methanol synthesis zone as part of the methanol synthesis product. If desired, carbon dioxide may be recovered from the methanol synthesis product, for example by conventional liquid/gas separation techniques.

Dimethyl ether present in synthesis gas passed to the methanol synthesis zone does not generally take part in the methanol synthesis reaction and is withdrawn from the methanol synthesis zone as part of the methanol synthesis product.

The methanol synthesis is accomplished in the presence of a methanol synthesis catalyst. At least a portion of the synthesis gas recovered from the carbonylation reaction product, and optionally at least a portion of synthesis gas recovered from the methanol synthesis product, is contacted in the methanol synthesis zone with a methanol synthesis catalyst to form a methanol synthesis product comprising methanol and unconverted synthesis gas.

A number of catalysts active for methanol synthesis are known in the art and are also available commercially, such as the Katalco™ series of methanol synthesis catalysts available from Johnson Matthey plc. Typically, the catalysts are based on copper and may also contain one or more additional metals such as zinc, magnesium and aluminium.

In one embodiment of this invention, the methanol synthesis catalyst comprises copper, zinc oxide and alumina.

The methanol synthesis catalyst may be employed in a fixed bed methanol synthesis zone, for example in the shape of pipes or tubes, where synthesis gas recovered from the carbonylation reaction product and optionally synthesis gas recovered from the methanol synthesis product are passed over or through the methanol synthesis catalyst.

The carbonylation reaction produces low boiling by-products which may form part of the synthesis gas recovered therefrom. Unexpectedly, it has now been found that these by-products do not require removal from the synthesis gas prior to its use in methanol synthesis. Without wishing to be bound by theory, it is believed that the by-products undergo hydrogenation in the methanol synthesis reaction, particularly in the presence of a methanol synthesis catalyst comprising copper, to form hydrogenated products which do not significantly deactivate the methanol synthesis catalyst. These hydrogenation products may be easily removed from the methanol synthesis zone, for example by purging. Thus, advantageously, integration of carbonylation and methanol synthesis processes avoids the need to remove the carbonylation by-products from synthesis gas prior to methanol synthesis and also mitigates the need for detrimental recycle of the by-products to the carbonylation reaction zone. Furthermore, it has been found that the formation of hydrogenation products has little, if any, significant effect on the space time yield to methanol synthesis product.

Synthesis gas recovered from the carbonylation reaction product may comprise carbonylation by-products in a total amount of 5 mol % or less, preferably 2 mol %, more preferably 1 mol % or less.

The by-products present in the synthesis gas recovered from the carbonylation reaction product may be one or more of olefins, for example ethylene, and $C_2$ oxygenate compounds, such as acetaldehyde and acetone, and are present in a total amount of less than 5 mol %, preferably less than 2 mol %, more preferably less than 1 mol %.

In an embodiment of the present invention, synthesis gas recovered from the carbonylation reaction product comprises ethylene and in an amount of 2 mol % or less, preferably 1 mol % or less.

In another embodiment, synthesis gas recovered from the carbonylation reaction product comprises $C_2$ oxygenate compounds selected from one or more of acetone and acetaldehyde and in a total amount of 2 mol % or less, preferably 1 mol % or less.

In a further embodiment of the present invention, synthesis gas recovered from the carbonylation reaction product comprising one or more low-boiling carbonylation by-products selected from ethylene, acetone and acetaldehyde, is passed to the methanol synthesis zone containing therein a methanol synthesis catalyst which is a methanol synthesis catalyst comprising copper, for example a catalyst comprising copper and at least one of zinc, aluminium and magnesium, preferably a copper/zinc oxide/alumina catalyst.

Carbonylation by-products present in the synthesis gas stream recovered from the carbonylation reaction product and passed to the methanol synthesis zone are hydrogenated in the presence of a methanol synthesis catalyst comprising copper to form hydrogenated by-products. The hydrogenated by-products may be removed from the system as part of a purge stream vented from the synthesis gas stream recovered from the methanol synthesis product.

In a preferred embodiment, synthesis gas recovered from the carbonylation reaction product comprising one or more low-boiling carbonylation by-products, selected from one or more of ethylene, acetone and acetaldehyde, is passed to the methanol synthesis zone and at least a portion of one or more of the by-products is hydrogenated in the methanol synthesis zone in the presence of a methanol synthesis catalyst, suitably a methanol synthesis catalyst comprising copper, preferably a catalyst comprising copper and at least one of zinc, aluminium and magnesium, most preferably a copper/zinc oxide/alumina catalyst, and at least a portion of the hydrogenated by-products are removed as part of a purge stream, suitably as part of a purge stream vented from the synthesis gas recovered from the methanol synthesis product.

Preferably, the methanol synthesis is carried out in the vapour phase.

Synthesis gas recovered from the carbonylation reaction product, and optionally synthesis gas recovered from the methanol synthesis product, is contacted with the methanol synthesis catalyst under reaction conditions effective to effect the conversion of synthesis gas to form a methanol synthesis product comprising methanol and unconverted synthesis gas.

Suitably, methanol synthesis is carried out at a temperature of from 210° C. to 300° C., such as in the range 210° C. to 270° C. or 220° C. to 300° C., for example in the range 230° C. to 275° C.

Preferably, the methanol synthesis is carried out at a total pressure in the range 25 to 150 barg, for example in the range 50 to 100 barg.

Suitably, the methanol synthesis is carried out at a temperature in the range in the range 230° C. to 275° C. and at a total pressure in the range 50 to 100 barg (5000 kPa to 10,000 kPa).

In an embodiment of the present invention, methanol synthesis is carried out at a temperature of from 210° C. to 270° C. and at a total pressure in the range 50 to 100 barg (5000 kPa to 10,000 kPa).

In a preferred embodiment, at least a portion of the synthesis gas recovered from the carbonylation reaction product, optionally combined with at least a portion of synthesis gas recovered from the methanol synthesis product, is contacted with a methanol synthesis catalyst based on copper, preferably a catalyst comprising copper, zinc and aluminium, at a temperature in the range 220° C. to 300° C. or 210° C. to 270° C. and at a total pressure in the range 25 to 150 barg (2500 kPa to 15,000 kPa).

Suitably, the total gas hourly space velocity of the total feed to the methanol synthesis zone (including any recycle synthesis gas, water and any imported carbon dioxide) is in the range 500 to 40,000 $h^{-1}$.

Contacting of the synthesis gas recovered from the carbonylation reaction product, and optionally synthesis gas recovered from the methanol synthesis product, with the methanol synthesis catalyst produces a methanol synthesis product comprising methanol and unconverted synthesis gas. Depending on the exact nature of the components of the synthesis gas feeds for methanol synthesis the methanol synthesis product in addition to methanol and synthesis gas may comprise one or more additional components such as carbon dioxide, water, dimethyl ether, inert gases and one or more hydrogenation products of ethylene, acetone and acetaldehyde, such as ethane, ethanol and propane respectively.

The methanol synthesis product is withdrawn from the methanol synthesis zone, preferably in vapour form.

Methanol may be recovered from one or more of the methanol synthesis product withdrawn from the methanol synthesis zone and the methanol-rich liquid stream recovered from the methanol synthesis product.

Methanol may be recovered from the withdrawn methanol synthesis product by known recovery techniques. Suitably, methanol may be recovered from at least a portion of the methanol synthesis product, for example by reducing the temperature of the methanol synthesis product to generate a cooled methanol-synthesis gas mixture. Suitably, the temperature of the mixture is reduced to a temperature in the range 30° C. to 50° C., preferably in the range 35° C. to 50° C. The cooled methanol-synthesis gas mixture is separated to recover a liquid methanol-rich product stream and a gaseous synthesis gas stream.

Preferably, substantially all of the methanol synthesis product is separated to recover a methanol-rich liquid stream and a synthesis gas stream.

Separation of at least a portion of the methanol synthesis product may be carried out in one or more separation units. Each of the separation unit(s) may be of conventional design and may comprise one or more heat exchange means to cool the methanol synthesis product to condense out liquid methanol together with other condensable components, such as water, from the methanol synthesis product and one or more gas/liquid separation means such as a knock-out drum or a tangential inlet drum, to separate the cooled methanol-synthesis gas mixture to recover a methanol-rich liquid stream and a gaseous synthesis gas stream.

Alternatively, separation of the methanol synthesis product may be carried out directly in the methanol synthesis zone, that is by withdrawing from the methanol synthesis zone one or more gaseous streams comprising synthesis gas and one or more liquid streams rich in methanol.

The methanol-rich liquid stream may comprise small amounts of water, unreacted dimethyl ether and inert gases. Methanol may be recovered from the methanol-rich liquid stream by conventional purification means, such as distillation, and sold as such or it may be used, for example, as a feedstock in a variety of chemical processes. For example, the methanol may be carbonylated with carbon monoxide in the presence of a Group VIII noble metal catalyst, such as rhodium, iridium or mixtures thereof, to form acetic acid.

Alternatively, the methanol may be dehydrated in the presence of a suitable catalyst to form dimethyl ether. Suitable catalysts include aluminas, such as gamma-alumina.

Dimethyl ether present in the methanol-rich liquid stream may be recovered therefrom, for example by distillation. The recovered dimethyl ether may be recycled to the carbonylation reaction zone.

The synthesis gas recovered from the methanol synthesis product may comprise carbon dioxide, minor amounts of water, methanol, dimethyl ether and the hydrogenation products, ethane and propane.

At least a portion of the synthesis gas recovered from the methanol synthesis product is recycled to the methanol synthesis zone. Suitably, 90% or more, such as 90 to 99%, of the synthesis gas may be recycled to the methanol synthesis zone.

If desired, to reduce the build-up of inert gases in the methanol synthesis zone a portion of the synthesis gas recovered from the methanol synthesis product may be vented as a purge stream. Suitably, 1 to 10% of the synthesis gas recovered from the methanol synthesis product may be vented as a purge stream.

Suitably, in each of the carbonylation reaction zone and the methanol synthesis zone, the reaction is conducted as a heterogeneous vapour phase reaction.

The integrated process of the present invention and its component methyl acetate and methanol production processes may each be operated as a continuous process or as a batch process, preferably the integrated process is operated as a continuous process.

FIG. 1 is a block diagram showing one embodiment of the present invention of an integrated process for the production of methyl acetate and methanol. The integrated unit 110 includes a synthesis gas feed line 112 and a dimethyl ether feed line 114 connected to a carbonylation reactor 116. The carbonylation reactor 116 contains a fixed bed of carbonylation catalyst, for example a mordenite zeolite, preferably H-mordenite. In use, fresh synthesis gas is heated to the desired carbonylation reaction temperature and fed to the carbonylation reactor 116 via synthesis gas feed line 112. The synthesis gas having a stoichiometric number in the range 0.9 to 1.3 comprises carbon monoxide, hydrogen and carbon dioxide. Dry dimethyl ether is fed to the carbonylation reactor 116 via dimethyl ether feed line 114. The dimethyl ether and synthesis gas are contacted with the catalyst in the carbonylation reactor 116 at a temperature in the range 250° C. to 350° C. and a total pressure in the range 10 to 100 barg (1000 kPa to 10,000 kPa), to form a gaseous carbonylation reaction product comprising methyl acetate and hydrogen-enriched synthesis gas. The carbonylation reaction product is withdrawn from the carbonylation reactor 116 via a carbonylation reaction product line 118, and fed to a separation unit 120 comprising, for example, a heat exchanger and knock-out drum. In separation unit 120, the carbonylation reaction product is cooled, preferably to a temperature in the range 40° C. to 50° C. and a methyl acetate-rich liquid stream and a synthesis gas stream are recovered from the separation unit 120. The methyl acetate-rich liquid stream is withdrawn from the separation unit 120 via a liquid product line 122. The synthesis gas stream is withdrawn from the separation unit 120 via a gaseous product line 124, heated in one or more heat exchangers (not shown) to the desired methanol synthesis temperature and passed in its entirety to a methanol reactor 126. The methanol reactor 126 contains a methanol synthesis catalyst, preferably, a methanol synthesis catalyst comprising copper, such as a Katalco™ commercial methanol synthesis catalyst available from Johnson Matthey plc. The synthesis gas is converted in the methanol reactor 126 under methanol synthesis conditions, for example at a temperature in the range 230° C. to 275° C. and a total pressure of 50 to 100 barg (5000 kPa to 10,000 kPa) to a methanol synthesis product comprising methanol and unconverted synthesis gas, which methanol synthesis product is withdrawn from the methanol reactor 126 via a methanol synthesis product line 128.

Figure 2:
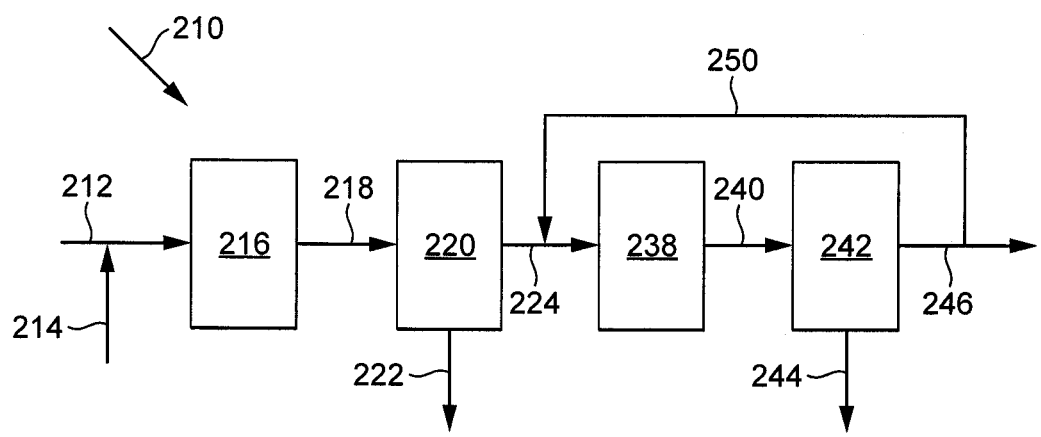
FIG. 2 is a block diagram showing an embodiment of the present invention of an integrated process for the production of methyl acetate and methanol and incorporating methanol product recovery.

FIG. 2 is a block diagram showing an embodiment of the present invention of an integrated process for the production of methyl acetate and methanol incorporating methanol product recovery and recycle to the methanol reactor of unconverted synthesis gas. The integrated unit 210 includes a synthesis gas feed line 212 and a dimethyl ether feed line 214 connected directly or indirectly to a carbonylation reactor 216. In use, synthesis gas is fed to the carbonylation reactor 216 via synthesis gas feed line 212. The synthesis gas comprises carbon monoxide, hydrogen and carbon dioxide. Dimethyl ether is fed to the carbonylation reactor 216 via dimethyl ether feed line 214, which joins the synthesis gas feed line 212 before entry to the carbonylation reactor 216. The carbonylation reactor 216 contains a carbonylation catalyst, for example a mordenite zeolite, preferably mordenite in its hydrogen form. A carbonylation reaction product comprising methyl acetate and hydrogen-enriched synthesis gas is withdrawn from the carbonylation reactor 216 via a carbonylation reaction product line 218. The carbonylation reaction product is supplied to a first separation unit 220 which comprises, for example, a heat exchanger and a knock-out drum. The carbonylation reaction product is separated in the first separation unit 220 to recover a methyl acetate-rich liquid stream and a synthesis gas stream. The methyl acetate-rich stream is withdrawn from the first separation unit 220 via a first liquid product line 222. The synthesis gas is withdrawn from the first separation unit 220 via a first gaseous product line 224, heated in one or more heat exchangers to the desired methanol synthesis temperature (not shown) and passed to a methanol reactor 238. The methanol reactor 238 contains a methanol synthesis catalyst preferably a methanol synthesis catalyst comprising copper, such as a Katalco™ commercial methanol synthesis catalyst available from Johnson Matthey plc. A methanol synthesis product comprising methanol and unconverted synthesis gas is withdrawn from the methanol reactor 238 via a methanol synthesis product line 240. The methanol synthesis product is supplied to a second separation unit 242 comprising, for example a heat exchanger and knock-out drum, where it is cooled and separated to recover a methanol-rich liquid stream and a synthesis gas stream. The methanol-rich liquid stream is withdrawn from the second separation unit 242 via a second liquid product line 244. The synthesis gas is withdrawn from the second separation unit 242 via a second gaseous product line 246, and is split into a first portion and a second portion, for example by a suitable valve system. The first portion of the synthesis gas is recycled to the methanol reactor 238 via a second gaseous product recycle line 250 which joins the first gaseous product feed line 224, so that the first portion of the synthesis gas is combined with the synthesis gas withdrawn from the separation unit 220, the combined feed is heated in one or more heat exchangers to the desired methanol synthesis temperature (not shown) and then passed to the methanol reactor 238. The second portion of the synthesis gas is vented as a purge gas. The first portion of the synthesis gas suitably comprises at least 90% of the synthesis gas withdrawn from the second separation unit 242, and the purge gas suitably comprises no more than 10% of the synthesis gas withdrawn from the second separation unit 242.

Figure 3:
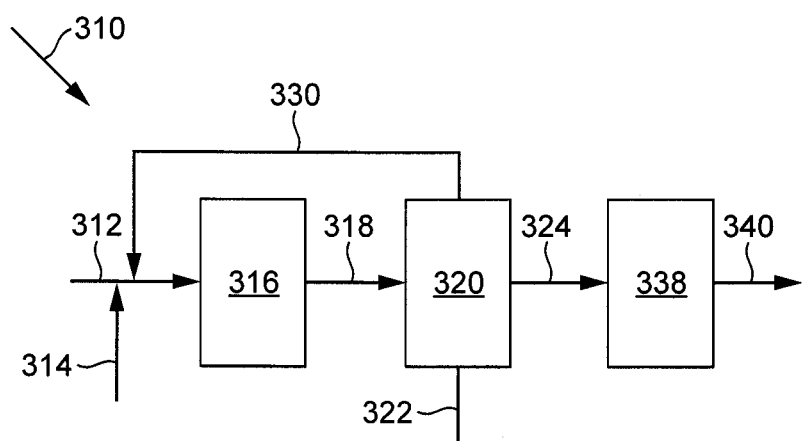
FIG. 3 is a block diagram showing an embodiment of the present invention of an integrated process for the production of methyl acetate and methanol and incorporating recycle to the carbonylation reactor of synthesis gas recovered from the carbonylation reaction product.

FIG. 3 is a block diagram showing an embodiment of the present invention of an integrated process for the production of methyl acetate and methanol and incorporating recycle to the carbonylation reactor of the synthesis gas recovered from the carbonylation reaction product. The integrated unit 310 includes a synthesis gas feed line 312 and a dimethyl ether feed line 314 connected directly or indirectly to a carbonylation reactor 316. In use, synthesis gas is fed to the carbonylation reactor 316 via synthesis gas feed line 312. The synthesis gas comprises carbon monoxide, hydrogen and carbon dioxide. Dimethyl ether is fed to the carbonylation reactor 316 via dimethyl ether feed line 314, which joins the synthesis gas feed line 312 before entry to the carbonylation reactor 316. The carbonylation reactor 316 contains a carbonylation catalyst, for example a mordenite zeolite, preferably mordenite in its hydrogen form. A gaseous carbonylation reaction product comprising methyl acetate and hydrogen-enriched synthesis gas is withdrawn from the carbonylation reactor 316 via a carbonylation reaction product line 318. The carbonylation reaction product is supplied to a first separation unit 320 which comprises, for example, a heat exchanger and a knock-out drum. The carbonylation reaction product is cooled and separated in the first separation unit 320 to recover a methyl acetate-rich liquid stream and a synthesis gas stream. The methyl acetate-rich liquid stream is withdrawn from the first separation unit 320 via a first liquid product line 322. The synthesis gas stream is withdrawn from the first separation unit 320 via a first gaseous product line 324, and is split into a first and a second portions, for example by a suitable valve system. The first portion of the synthesis gas stream is heated in one or more heat exchangers to the desired methanol synthesis temperature (not shown) and passed to a methanol reactor 338, and the second portion of the synthesis gas stream is recycled to the carbonylation reactor 316 via a first gaseous product recycle line 330. The first portion of the synthesis gas stream suitably comprises less than 50% of the synthesis gas withdrawn from the first separation unit 320, for example 20 to 30%, and the second portion of the synthesis gas stream suitably comprises more than 50%, for example 70 to 80%, of the synthesis gas stream withdrawn from the first separation unit 320. The methanol reactor 338 contains a methanol synthesis catalyst, preferably a methanol synthesis catalyst comprising copper, such as such as a Katalco™ commercial methanol synthesis catalyst available from Johnson Matthey plc. A methanol synthesis product stream comprising methanol and unconverted synthesis gas is withdrawn from the methanol reactor 338 via a methanol synthesis product line 340.

Figure 4:
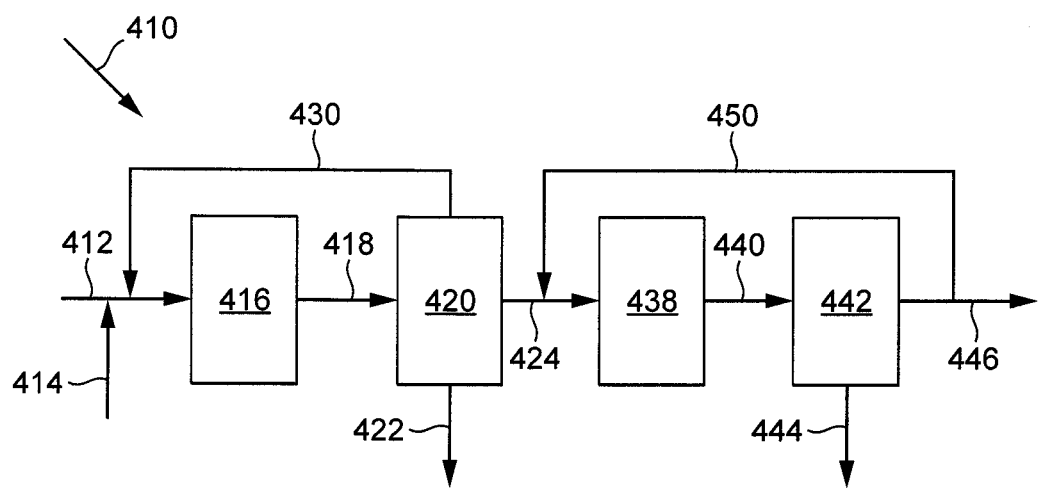
FIG. 4 is a block diagram showing an embodiment of the present invention of an integrated process for the production of methyl acetate and methanol and incorporating recycle to the carbonylation reactor of synthesis gas recovered from the carbonylation reaction product, methanol product recovery and recycle to the methanol reactor of unconverted synthesis gas.

FIG. 4 is a block diagram showing an embodiment of the present invention of an integrated process for the production of methyl acetate and methanol and incorporating recycle to the carbonylation reactor of the synthesis gas stream, methanol product recovery and recycle to the methanol reactor of unconverted synthesis gas. The integrated unit 410 includes a synthesis gas feed line 412 and a dimethyl ether feed line 414 connected directly or indirectly to a carbonylation reactor 416. In use, synthesis gas is fed to the carbonylation reactor 416 via synthesis gas feed line 412. The synthesis gas comprises carbon monoxide, hydrogen and carbon dioxide. Dimethyl ether is fed to the carbonylation reactor 416 via dimethyl ether feed line 414, which joins the synthesis gas feed line 412 before entry to the carbonylation reactor 416. The carbonylation reactor 416 contains a carbonylation catalyst, for example a mordenite zeolite, such as mordenite in its hydrogen form. A gaseous carbonylation reaction product comprising methyl acetate and hydrogen-enriched synthesis gas is withdrawn from the carbonylation reactor 416 via a carbonylation reaction product line 418. The carbonylation reaction product also comprises unreacted dimethyl ether and small amounts of methanol and water. The carbonylation reaction product is passed to a first separation unit 420 which comprises, for example, a heat exchanger and a knock-out drum. The carbonylation reaction product is cooled and separated in the first separation unit 420 to recover a methyl acetate-rich liquid stream comprising mainly methyl acetate together with small amounts of dimethyl ether, water and methanol, and a synthesis gas stream comprising mainly synthesis gas with small amounts of methyl acetate and dimethyl ether. The methyl acetate-rich liquid stream is withdrawn from the first separation unit 420 via a first liquid product line 422. The synthesis gas is withdrawn from the first separation unit 420 via a first gaseous product line 424, and is split into a first and a second portion, for example by a suitable valve arrangement. The first portion of the synthesis gas is heated in one or more heat exchangers to the desired methanol synthesis temperature (not shown) and passed to a methanol reactor 438, and the second portion of the synthesis gas is recycled to the carbonylation reactor 416 via a first gaseous product recycle line 430. The first portion of the synthesis gas suitably comprises less than 50%, for example 20 to 30%, of the synthesis gas, and the second portion of the synthesis gas suitably comprises more than 50%, for example 70 to 80%, of the synthesis gas. The methanol reactor 438 contains a methanol synthesis catalyst for example, a methanol synthesis catalyst comprising copper, such as a Katalco™ commercial catalyst available from Johnson Matthey plc. A methanol synthesis product comprising methanol, unconverted synthesis gas, and minor amounts of water and dimethyl ether is withdrawn from the methanol reactor 438 via a methanol product line 440. The methanol synthesis product is supplied to a second separation unit 442 comprising, for example, a heat exchanger and knock-out drum, where it is cooled to a temperature suitably in the range 35° C. to 50° C. and separated to recover a methanol-rich liquid stream comprising mainly methanol together with small amounts of one or more of water and dimethyl ether, and a synthesis gas stream comprising mainly carbon monoxide, hydrogen and carbon dioxide and small amounts of one or more of dimethyl ether, water and methanol. The methanol-rich liquid stream is withdrawn from the second separation unit 442 via a second liquid product line 444. The synthesis gas stream is withdrawn from the second separation unit 442 via a gaseous product line 446, and is split into a first portion and a second portion, for example by a suitable valve system. The first portion of the synthesis gas is recycled to the methanol reactor 438 via a synthesis gas recycle line 450 which joins the first gaseous product line 424, so that the first portion of the synthesis gas is combined with the synthesis gas withdrawn from the first separation unit 420, heated in one or more heat exchangers to the desired methanol synthesis temperature (not shown) and then passed to the methanol reactor 438. The second portion of the synthesis gas withdrawn from the second separation unit 442 is vented as a purge gas. The first portion of the synthesis gas suitably comprises at least 90% of the synthesis gas withdrawn from the second separation unit 442, and the second portion of the synthesis gas suitably comprises less than 10% of the synthesis gas withdrawn from the second separation unit 442.

The invention is now illustrated with reference to the following non-limiting Examples.

EXAMPLE 1

This Example demonstrates an integrated process for the production of methyl acetate and methanol, wherein a gaseous stream obtained from the carbonylation of dimethyl ether to produce methyl acetate is used as the feed to the methanol synthesis reaction. FIG. 1 shows the basic components suitable for carrying out the integrated process of this Example.

A synthesis gas comprising hydrogen, carbon monoxide, carbon dioxide and inert gases with a hydrogen:carbon monoxide molar ratio of 1.15 and a stoichiometric number (SN) of 1.07, and comprising trace quantities of inert gases (Syngas Feed), is fed to a carbonylation reactor. Dimethyl ether (DME Feed) is fed to the carbonylation reactor. The carbonylation reaction is conducted in the carbonylation reactor as a fixed bed vapour-phase process utilising H-mordenite zeolite as catalyst and is operated under conditions effective to catalyse the carbonylation of the dimethyl ether to produce methyl acetate, for example at a temperature in the range 250° C. to 350° C. and a total pressure in the range 10 to 100 barg (1000 kPa to 10,000 kPa). The gaseous carbonylation reaction product withdrawn from the carbonylation reactor comprising methyl acetate and hydrogen-enriched synthesis gas is cooled to a temperature in the range 40° C. to 50° C. and separated in a gas/liquid separator to recover a liquid stream rich in methyl acetate (Methyl Acetate Stream) and a gaseous stream comprising synthesis gas (Syngas Feed (to methanol synthesis)). The synthesis gas stream has a stoichiometric number of 2.04, is heated to the methanol synthesis temperature and passed to a conventional methanol synthesis reactor. The methanol synthesis is a low pressure synthesis operated at a total pressure of 50 to 100 barg (5000 kPa to 10,000 kPa), a temperature of from 230° C. to 275° C., and employing a commercially available methanol synthesis catalyst comprising copper, such as Katalco™ methanol synthesis catalysts, available from Johnson Matthey plc, to produce a methanol synthesis product stream (Methanol Synthesis Product) comprising methanol and unconverted synthesis gas.

Examples of the molar flow rates that may be obtained in the above integrated process are given in Table 1 below.

TABLE 1

| Molar Flow per unit time | Syngas Feed (to carbonylation) | DME Feed (to carbonylation) | Methyl Acetate Stream | Syngas Feed (to methanol synthesis) | Methanol Synthesis Product |
|---|---|---|---|---|---|
| Hydrogen | 2323 | | | 2323 | 313 |
| Carbon monoxide | 2020 | | | 1020 | 30 |
| Carbon dioxide | 81 | | | 81 | 71 |
| Inerts | 101 | | | 101 | 101 |
| Dimethyl ether | | 1000 | | | |
| Methyl acetate | | | 1000 | | |
| Methanol | | | | | 1000 |
| Hydrogen:carbon monoxide molar ratio | 1.15 | | | 2.28 | |
| Stoichiometric number (SN) | 1.07 | | | 2.04 | |

EXAMPLE 2

This Example demonstrates an integrated process for the production of methyl acetate and methanol, wherein a gaseous stream obtained from the carbonylation of dimethyl ether to produce methyl acetate is used as the feed to the methanol synthesis reaction, and wherein the product stream obtained from the methanol synthesis reaction system is separated into a liquid stream comprising methanol and a gaseous stream. FIG. 2 shows the basic components suitable for carrying out the integrated process of this Example.

The process of Example 1 is repeated using a synthesis gas (Synthesis Gas Feed) and a dimethyl ether feed (DME Feed) having the compositions set out in Table 2. The product stream from the methanol synthesis is supplied to a separation unit, comprising a heat exchanger and a knock-out drum, cooled and separated into a liquid methanol-rich stream (Methanol Liquid Stream) and a synthesis gas stream (Methanol Gaseous Stream).

Examples of the molar flow rates that may be obtained in the above integrated process are given in Table 2 below.

TABLE 2

| Molar Flow per unit time | Syngas Feed (to carbonylation) | DME Feed (to carbonylation) | Methyl Acetate Stream | Syngas Feed (to methanol synthesis) | Methanol Liquid Stream | Methanol Gaseous Stream |
|---|---|---|---|---|---|---|
| Hydrogen | 2323 | | | 2323 | | 313 |
| Carbon monoxide | 2020 | | | 1020 | | 30 |
| Carbon dioxide | 81 | | | 81 | | 71 |
| Inerts | 101 | | | 101 | | 101 |
| Dimethyl ether | | 1000 | | | | |
| Methyl acetate | | | 1000 | | | |
| Methanol | | | | | 1000 | |
| Hydrogen:carbon monoxide molar ratio | 1.15 | | | 2.28 | | 10 |
| Stoichiometric number (SN) | 1.07 | | | 2.04 | | 2.40 |

EXAMPLE 3

This Example investigates the effect of low-boiling by-products obtained from the carbonylation of dimethyl ether to produce methyl acetate on a methanol synthesis reaction. Pellets of Katalco™ methanol synthesis catalyst (Johnson Matthey plc) were crushed and sieved to a size-fraction of 125-160 microns. A tubular reactor of 9 mm internal diameter was charged with 3 ml of the catalyst diluted 1:1 v/v with quartz chips. The length of the catalyst bed was 100 mm. A gas composition of 62 vol % $H_2$, 7 vol % CO, 5 vol % $CO_2$, 5 vol % Ar and 20 vol % N2, and a co-feed of ethylene (1 vol %), were fed to the reactor at total gas hourly space velocities (GHSV) of 5000 $h^{-1}$, 7600 $h^{-1}$, 10000 $h^{-1}$, 12500 $h^{-1}$ and 20000 $h^{-1}$ at a pressure of 75 bar (7500 kPa) and a temperature of 260° C. over a period of 52 hours. The exit stream from the reactor was passed to two gas chromatographs (GC's) for analysis of the components of the exit stream. The GC's were a Varian 4900 micro GC with three columns (molecular sieve 5A, Porapak®Q and CP-Wax-52), each column equipped with a thermal conductivity detector and an Interscience trace GC with two columns (CP Sil 5 and CP-Wax-52), each column equipped with a flame ionization detector.

Figure 5:
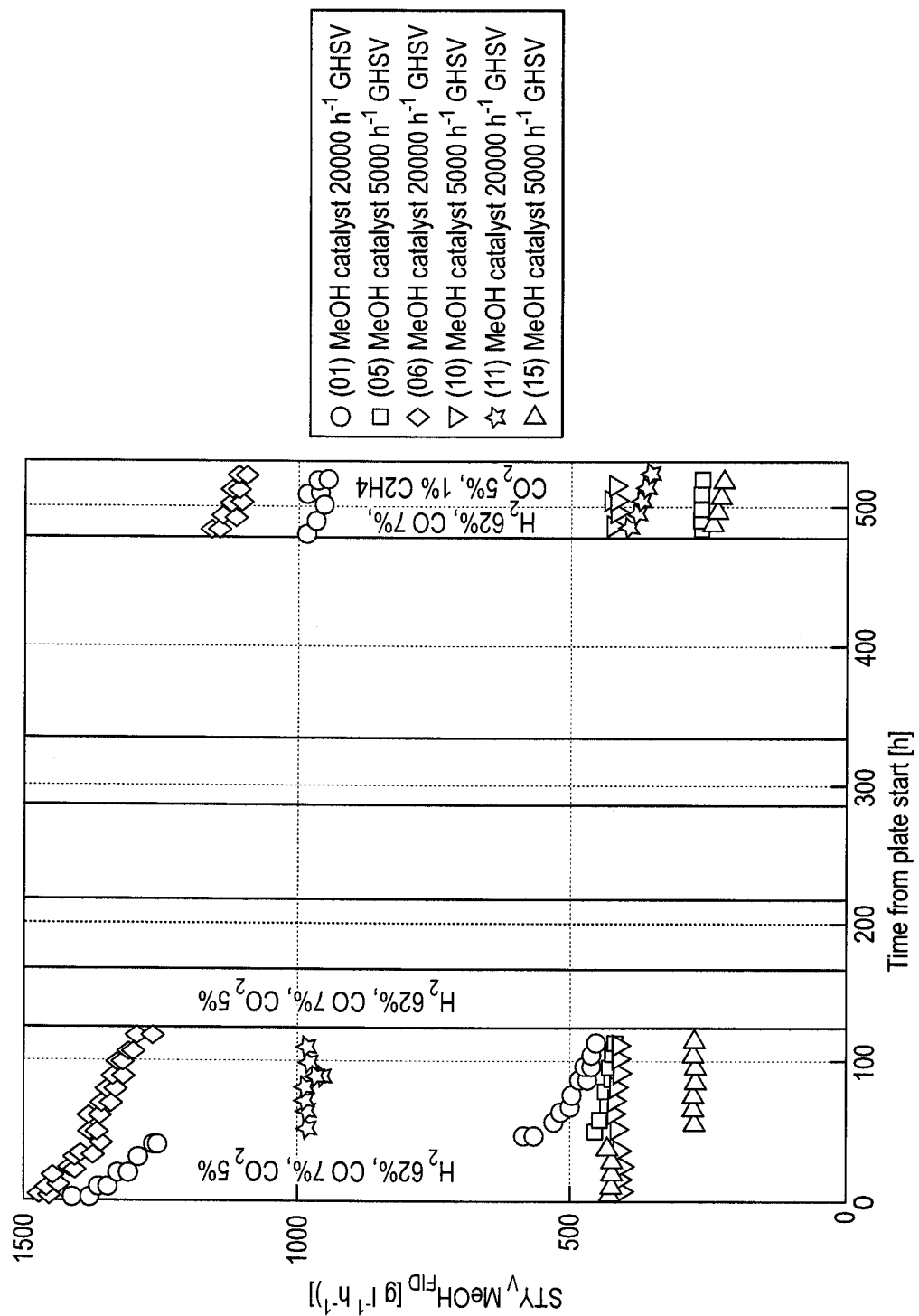
FIG. 5 illustrates the effect of ethylene on methanol productivity in methanol synthesis.
Figure 6:
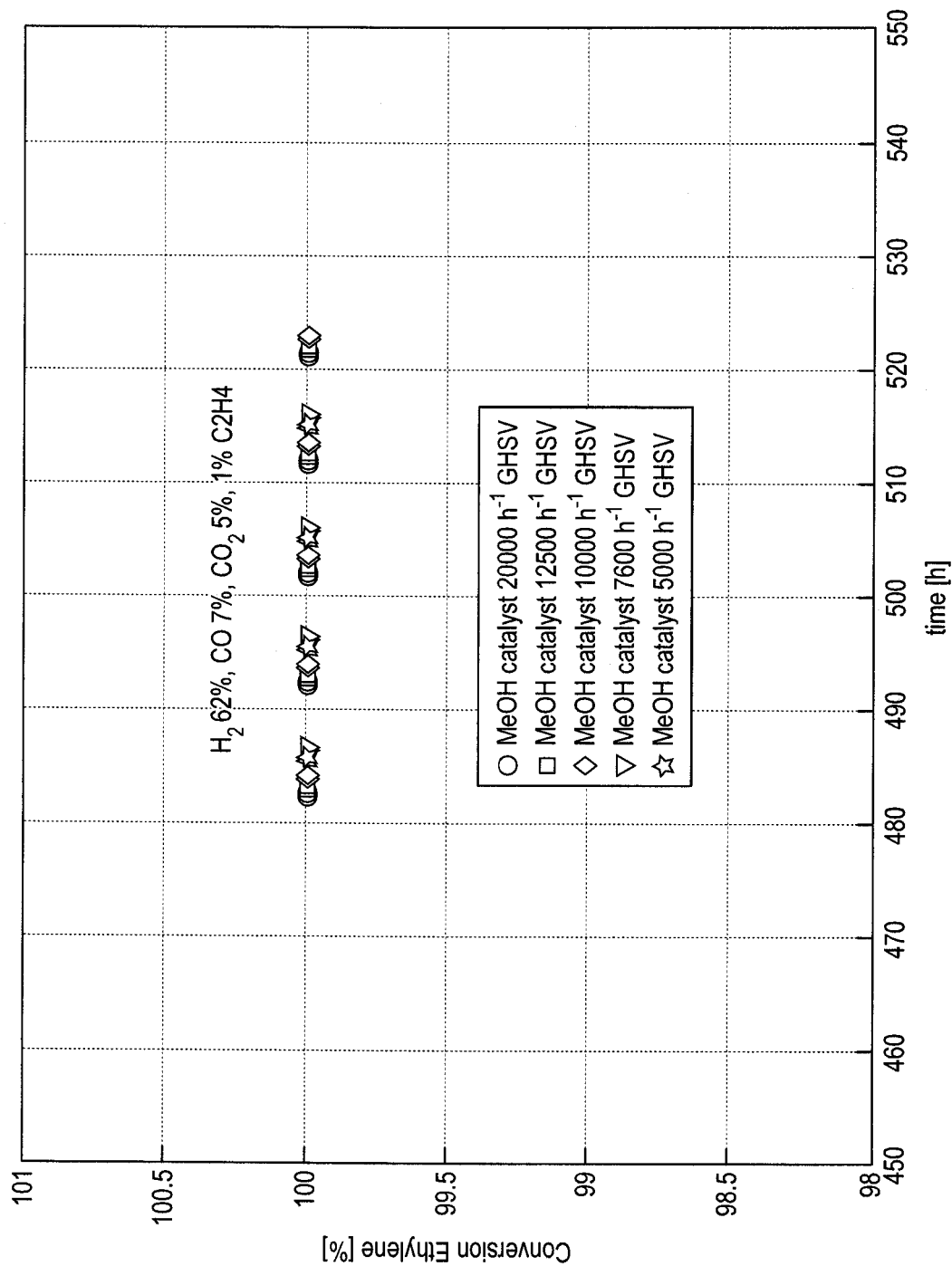
FIG. 6 illustrates the degree of conversion of ethylene during methanol synthesis.

The results of this Example are illustrated in FIGS. 5 and 6. The productivity in grams of methanol product per litre of catalyst per hour, at each of the GHSV's is indicated in FIG. 5. The degree of conversion of ethylene during methanol synthesis at each of the GHSV's is indicated in FIG. 6. The data in FIG. 5 and FIG. 6 indicates that the productivity to methanol was not affected by the feeding of ethylene into the methanol synthesis reaction and that the conversion of ethylene therein was complete.

EXAMPLE 4

This Example demonstrates an integrated process for the production of methyl acetate and methanol, wherein part of the gaseous stream obtained from the carbonylation of dimethyl ether to produce methyl acetate is used as the feed to the methanol synthesis reaction. FIG. 4 shows the basic components suitable for carrying out the integrated process of this Example.

The carbonylation reaction detailed in Example 1 is repeated using a synthesis gas (Syngas Feed) and a dimethyl ether feed (DME Feed) having the compositions set out in Table 3. The synthesis gas has a hydrogen:carbon monoxide molar ratio of 1.14 and a stoichiometric number (SN) of 1.03. The synthesis gas and the dimethyl ether are combined before being introduced into the carbonylation reactor. The gaseous product stream from the carbonylation reactor (Product stream (Carb)) is supplied to a separation unit and cooled and separated into a liquid stream comprising predominantly methyl acetate (MeOAc liquid stream), and a gaseous stream comprising mainly synthesis gas together with unreacted dimethyl ether and methyl acetate (Syngas stream). The stoichiometric number of the gaseous stream is 2.05. The gaseous stream is split into two streams, with approximately 76% of the gaseous stream (Recycle syngas stream (to Carb)) being recycled to the carbonylation reactor to produce a combined feed (Total Feed (to Carb)), and approximately 24% of the gaseous stream is passed to a conventional methanol synthesis reactor in combination with a recycled stream (Recycle syngas stream (to Methanol)) from the methanol synthesis, to form a combined feed (Total Feed (to Methanol)). The combined feed is heated in one or more heat exchangers to the methanol synthesis temperature and passed to the methanol synthesis reactor, and contacted therein with a commercial methanol synthesis catalyst comprising copper, such as Katalco™ available from Johnson Matthey plc. The methanol synthesis is a low pressure synthesis operated at a temperature of from 230° C. to 275° C. and a total pressure of 50 to 100 barg to produce a product stream comprising methanol (Product stream (Methanol)). The product stream from the methanol synthesis is withdrawn therefrom and supplied to a conventional separation unit comprising a heat exchanger and a knockout drum, and cooled and separated to recover a methanol-rich liquid stream (Methanol liquid stream) and a synthesis gas stream (Syngas stream (Methanol)). Approximately 2% of the synthesis gas stream is vented as a purge gas (Purge (Methanol)) and the remaining portion (approximately 98%) of the synthesis gas stream is recycled to the methanol synthesis reactor (Recycle syngas stream (to Methanol)).

Examples of the molar flow rates that may be obtained in the above integrated process are given in Table 3 below.

TABLE 3

| Molar Flow per unit time | Syngas Feed | DME Feed | Recycle syngas stream (to Carb) | Total Feed (to Carb) | Product stream (Carb) | MeOAc liquid stream | Syngas stream (Carb) | Recycle syngas stream (to Methanol) | Total Feed (to Methanol) | Product stream (Methanol) | Methanol liquid stream | Syngas stream (Methanol) | Purge (Methanol) |
|---|---|---|---|---|---|---|---|---|---|---|---|---|---|
| $H_2$ | 225.2 | 0 | 700.1 | 925.3 | 921.3 | 2.4 | 918.9 | 619.1 | 837.9 | 632.6 | 0.9 | 631.7 | 12.6 |
| $CH_4$ | 2.0 | 0 | 18.2 | 20.2 | 24.2 | 0.3 | 23.9 | 221.0 | 226.7 | 226.7 | 1.2 | 225.5 | 4.5 |
| $N_2$ | 1.0 | 0 | 3.1 | 4.1 | 4.1 | 0 | 4.1 | 44.7 | 45.6 | 45.6 | 0.1 | 45.6 | 0.9 |
| CO | 198.4 | 0 | 307.9 | 506.3 | 406.3 | 2.2 | 404.1 | 68.1 | 164.3 | 69.6 | 0.1 | 69.5 | 1.4 |
| $H_2O$ | 0 | 0 | 0.8 | 0.9 | 2.9 | 1.7 | 1.1 | 0.2 | 0.5 | 5.8 | 5.6 | 0.2 | 0 |
| $CO_2$ | 9.9 | 0 | 23.1 | 33.0 | 33.0 | 2.7 | 30.4 | 43.5 | 50.7 | 45.4 | 1.0 | 44.4 | 0.9 |
| MeOH | 0 | 0.1 | 0 | 0.1 | 0.1 | 0.1 | 0 | 8.2 | 8.2 | 108.2 | 99.8 | 8.4 | 0.2 |
| MeOAc | 0 | 0 | 13.8 | 13.8 | 113.8 | 95.7 | 18.2 | 1.6 | 5.9 | 5.9 | 4.3 | 1.6 | 0 |
| DME | 0 | 121.5 | 19.9 | 141.4 | 39.4 | 13.3 | 26.2 | 15.0 | 21.2 | 21.2 | 5.9 | 15.3 | 0.3 |
| Total | 436.5 | 121.6 | 1087.1 | 1645.2 | 1545.2 | 118.4 | 1426.8 | 1021.3 | 1361.0 | 1161.0 | 118.9 | 1042.1 | 20.8 |
| $H_2$:CO | 1:14 | | 2.27 | 1.83 | 2.27 | | 2.27 | 9.09 | 5.10 | 9.09 | | 9.09 | 9.09 |
| SN | 1.03 | | 2.05 | 1.65 | 2.02 | | 2.05 | 5.16 | 3.66 | 5.10 | | 5.16 | 5.16 |

The abbreviations used in Table 3 have the following meanings: -
DME is dimethyl ether
MeOH is methanol
MeOAc is methyl acetate
SN is stoichiometric number

The invention claimed is:

1. An integrated process for the production of methyl acetate and methanol which process comprises:
   (i) feeding synthesis gas and dimethyl ether into a carbonylation reaction zone and reacting therein the dimethyl ether and synthesis gas in the presence of a carbonylation catalyst to form a gaseous carbonylation reaction product comprising methyl acetate and a hydrogen-enriched synthesis gas relative to the hydrogen content of the feed synthesis gas and wherein the carbonylation catalyst is an aluminosilicate zeolite which comprises at least one channel which is defined by an 8-membered ring;
   (ii) withdrawing carbonylation reaction product from the carbonylation reaction zone and recovering from at least a portion of the carbonylation reaction product a methyl acetate-rich liquid stream and a synthesis gas stream in which ethylene is present in an amount of 2 mol % or less; and
   (iii) passing at least a portion of the synthesis gas stream recovered from the carbonylation reaction product to a methanol synthesis zone and contacting it therein with a methanol synthesis catalyst to form a methanol synthesis product comprising methanol and unconverted synthesis gas and hydrogenated ethylene.

2. A process according to claim 1 which further comprises the steps of
   (iv) withdrawing methanol synthesis product from the methanol synthesis zone and recovering therefrom a methanol-rich liquid stream and a synthesis gas stream; and
   (v) recycling at least a portion of the synthesis gas stream recovered from the methanol synthesis product to the methanol synthesis zone.

3. A process according to claim 1 wherein the synthesis gas feed to the carbonylation reaction zone has a stoichiometric number, SN where $SN=(H_2-CO_2)/(CO+CO_2)$ which is lower than the stoichiometric number of the synthesis gas stream recovered from the carbonylation reaction product.

4. A process according to claim 1 wherein the synthesis gas feed to the carbonylation reaction zone has a stoichiometric number in the range 0.9 to 1.3.

5. A process according to claim 1 wherein the synthesis gas feed to the carbonylation reaction zone is selected from fresh synthesis gas and a mixture of fresh and recycle synthesis gas.

6. A process according to claim 1 wherein the synthesis gas feed (including any recycles) to the carbonylation reaction zone comprises carbon dioxide.

7. A process according to claim 6 wherein carbon dioxide is present in the synthesis gas in an amount 0.5 to 12 mol %.

8. A process according to claim 1 wherein the aluminosilicate zeolite has a framework structure type selected from MOR, FER, OFF and GME.

9. A process according to claim 8 wherein the framework structure type is MOR and the zeolite is a mordenite.

10. A process according to claim 1 wherein synthesis gas and dimethyl ether are reacted in the carbonylation reaction zone under conditions of a temperature in the range 250° C. to 350° C. and a total pressure in the range 50 to 100 barg (5000 kPa to 10,000 kPa).

11. A process according to claim 1 wherein synthesis gas recovered from the carbonylation reaction product is split into two portions.

12. A process according to claim 11 wherein the synthesis gas is split into a major portion and a minor portion and wherein the major portion is recycled to the carbonylation reaction zone and the minor portion is passed to the methanol synthesis zone.

13. A process according to claim 12 wherein the major portion is 70 to 80 mol % of the synthesis gas.

14. A process according to claim 12 wherein the minor portion is 10 to 30 mol % of the synthesis gas.

15. A process according to claim 10 wherein at least a portion of the synthesis gas stream recovered from the methanol synthesis product is passed to the methanol synthesis zone as a combined feed with the synthesis gas stream recovered from the carbonylation reaction product.

16. A process according to claim 1 wherein synthesis gas passed to the methanol synthesis zone further comprises one or more carbonylation by-products selected from acetone and acetaldehyde.

17. A process according to claim 16 wherein at least a portion of the by-products are hydrogenated in the methanol synthesis zone in the presence of a methanol synthesis catalyst.

18. A process according to claim 17 wherein at least a portion of the hydrogenated by-products are removed as part of a purge stream vented from the synthesis gas stream recovered from the methanol synthesis product.

19. A process according to claim 1 wherein the methanol synthesis catalyst comprises copper.

20. A process according to claim 1 wherein synthesis gas is contacted with the methanol synthesis catalyst under conditions of a temperature of from 210° C. to 270° C. and a total pressure in the range 50 to 100 barg (5000 kPa to 10,000 kPa).

21. A process according to claim 1 wherein there is introduced into the methanol synthesis zone one or more of water and imported carbon dioxide.

22. A process according to claim 2 wherein the methanol-rich liquid stream comprises dimethyl ether, dimethyl ether is recovered therefrom and the recovered dimethyl ether is recycled to the carbonylation reaction zone.

23. A process according to claim 1 wherein methanol is recovered from the methanol synthesis product withdrawn from the methanol synthesis zone.

24. A process according to claim 2 wherein methanol is recovered from the methanol-rich liquid stream recovered from the methanol synthesis product.

25. A process according to claim 2 wherein a purge stream is vented from the synthesis gas stream recovered from the methanol synthesis product.

26. A process according to claim 1 wherein methyl acetate is recovered from at least a portion of the methyl acetate-rich liquid stream and the recovered methyl acetate is converted to acetic acid.

27. A process according to claim 26 wherein recovered methyl acetate is converted to acetic acid by hydrolysis.

28. A process according to claim 1 wherein in each of the carbonylation reaction zone and the methanol synthesis zone, the reaction is conducted as a heterogeneous vapour phase reaction.

29. A process according to claim 1 wherein the process is operated as a continuous process.

* * * * *